US006831733B2

(12) United States Patent
Pettersson et al.

(10) Patent No.: US 6,831,733 B2
(45) Date of Patent: Dec. 14, 2004

(54) ANALYSIS METHOD AND SYSTEM THEREFOR

(75) Inventors: Joakim Pettersson, Ängelholm (SE); Johnny Svensson, Ängelholm (SE)

(73) Assignee: Hemocue AB, Ängelholm (SE)

( * ) Notice: Subject to any disclaimer, the term of this patent is extended or adjusted under 35 U.S.C. 154(b) by 102 days.

(21) Appl. No.: 10/323,755

(22) Filed: Dec. 20, 2002

(65) Prior Publication Data

US 2003/0123047 A1 Jul. 3, 2003

(30) Foreign Application Priority Data

Dec. 28, 2001 (SE) .............................................. 0104443

(51) Int. Cl.⁷ .............................................. G01N 33/48
(52) U.S. Cl. ...................................... 356/39; 600/320
(58) Field of Search .............................. 356/39, 40, 41, 356/335–343, 436; 600/320, 321

(56) References Cited

U.S. PATENT DOCUMENTS

| 3,961,346 A | | 6/1976 | White |
| 4,088,448 A | | 5/1978 | Lilja et al. |
| 4,997,769 A | | 3/1991 | Lundsgaard |
| 5,064,282 A | | 11/1991 | Curtis |
| 5,385,539 A | | 1/1995 | Maynard |
| 5,601,080 A | | 2/1997 | Oppenheimer |
| 5,674,457 A | | 10/1997 | Williamsson et al. |
| 5,773,301 A | * | 6/1998 | Ziegler .......................... 436/66 |
| 5,866,349 A | | 2/1999 | Lilja et al. |
| 5,898,487 A | | 4/1999 | Hage |
| 6,064,474 A | | 5/2000 | Lee et al. |
| 6,103,197 A | * | 8/2000 | Werner ..................... 422/82.09 |
| 6,262,798 B1 | | 7/2001 | Shepherd et al. |

FOREIGN PATENT DOCUMENTS

| WO | WO 88/01376 | 2/1988 |
| WO | WO 01/53806 | 7/2001 |
| WO | WO 02/01195 | 1/2002 |

OTHER PUBLICATIONS

Journal of Clinical Monitoring and Computing, vol. 15, Nos. 3 to 4, *Evaluation of the HB–Quick®: A Portable Hemoglobinometer*, Alice K. Kong, MD et al., May 1999, pp. 172 to 177.
Bulletin, No. 15–1999, Nov. 1999, *Measuring Bilirubin on Whole Blood*, Ingrid Fussing Ph.D., pp. 3 to 11.
Analyst, vol. 123, Mar. 1998, Caicai Wu et al.: "*Feasibility study of the spectroscopic measurement of oxyhemoglobin using whole blood without pre–treatment*", pp. 477 to 481.

* cited by examiner

*Primary Examiner*—Frank G. Font
*Assistant Examiner*—Roy M. Punnoose
(74) *Attorney, Agent, or Firm*—Burns, Doane, Swecker & Mathis, L.L.P.

(57) ABSTRACT

The invention concerns a method for quantitative hemoglobin determination in undiluted, unhemolyzed whole blood comprising the steps of:

providing a disposable, capillary, which has an optical path length of less than 1 mm;

filling said cuvette with a sample of unaltered whole blood;

performing a first absorption measurement at a wavelength in the range 490–520 nm directly on the sample in the cuvette, and further conducting a second absorption measurement, and processing results of the first and second absorption measurements to determine the concentration of hemoglobin in the sample, wherein the step of processing comprises compensating for scattering in the sample, said compensating being dependent on the result of the second absorption measurement.

A system for implementing the method is also disclosed.

35 Claims, 4 Drawing Sheets

ANALYSIS METHOD AND SYSTEM THEREFOR

FIELD OF INVENTION

The present invention concerns an analysis method and a system for performing this analysis. Specifically the invention concerns a method for determination of hemoglobin in unaltered whole blood and a system which can be used in this determination.

BACKGROUND ART

A disposable cuvette for sampling a fluid, mixing the sample with a reagent and directly making optical analyses of the sample mixed with the reagent is previously known from U.S. Pat. No. 4,088,448. This known cuvette has several advantages as it i.a. simplifies the sampling procedure, reduces the number of utensils and considerably improves the accuracy of analysis by making the analysing procedure independent of the operating technique of the operator making the analysis. A cuvette construction based on the same principle and with improved flow characteristics is disclosed in the U.S. Pat. No. 5,674,457.

A disposable cuvette developed according to these patents is currently widely used for hemoglobin measurement (Hb determination) of undiluted whole blood. To this end the cuvette cavity has been pre-treated with a reagent, such that when a blood sample is drawn into the cuvette, the walls of the red blood cells are disintegrated and a chemical reaction is initiated. The result of the reaction allows Hb determination by absorption measurement directly through the transparent walls of the cuvette which, in the measuring zone, also called the optical window, has a predetermined and accurately defined distance between the inner surfaces of the opposing planar walls. The measurement method is based on a modified azidmethemoglobin method according to Vanzetti, G., Am.J. Lab. & Clin. Med. 67, 116 (1966).

The spectrophotometric measurements are made at 570 and 880 nm. This quantitative measurement method based on dry chemistry has met with considerable success as can be seen in e.g. the article by von Schenck et al in Clinical Chemistry, vol 32, No 3, 1986 as the method gives equal or even superior results in comparison with the results obtained with standardised wet methods for the determination of Hb. The reagent used is comprised of sodium deoxycholate which hemolyses the red blood cells, sodium azide and sodium nitrite, which converts hemoglobin to azidmethemoglobin.

Due to the hygroscopic properties of the reagents used, the shelf life is limited and the storage of the cuvettes in sealed packages including a drying agent is required. Even more troublesome is the fact that, in climates with high humidity, the cuvette has to be used within a few minutes after the removal from the package, as otherwise the reagents will be destroyed and the measurement will be inaccurate and thus useless.

The problems originating from the hygroscopic properties of the reagents used may however be eliminated as it has been found that these reagents must not be used as disclosed in the co-pending patent application PCT SE01/01442 according to which the first absorption measurement is performed at a wavelength range 490–520 nm directly on the sample in the microcuvette. According to the invention disclosed in this patent application it is however necessary that the blood is hemolysed before the measurement is performed. The cuvette cavity must thus include a hemolysing agent for disintegrating the red blood cells and releasing the hemoglobin contained in these cells. The necessity of using a hemolysing agent when performing photometric absorbance measurements of hemoglobin in a blood sample is also disclosed in e.g. the U.S. Pat. No. 5,064,282 (Artel).

Quantitative methods for optical determination of hemoglobin in whole blood without using hemolysing agent are known but these methods have in common that they are all comparatively complicated. This depends above all on the inhomogeneity of the blood due to the high concentration of red blood cells, a consequence of which is that light is scattered upon interaction with these particles of inhomogeneous blood samples. Accordingly the light is not transmitted directly through the sample but deflected over a range of scattering angles. Another factor that causes problems is the fact that blood may contain as many as five different species of hemoglobin. Patent publications addressing these problems are i.a. the U.S. Pat. No. 6,262,798 (Shepherd) and WO 01/53806 (Radiometer).

According to the invention disclosed in the U.S. Pat. No. 6,262,798 a plurality of wavelengths are needed in order to achieve a correct measurement. The fact that many wavelengths are needed makes the spectrophotometer comparatively complicated. The wavelengths are selected by their ability to distinguish the hemoglobin species at minimum scatter and maximum absorbance. The patent also discloses the use of a large detector which reduces the problem of scattering beyond the detection range.

WO 01/53806 discloses an apparatus which is especially applicable for optical measurements on whole blood. This apparatus comprises an absorption filter or an interference filter, which provides correction for variations in the detector sensitivity and in the effective optical path length as observed upon varying level of scattering. The apparatus uses a large detector for detecting scattered light transmitted through the absorption filter or the interference filter.

The finding according to the present invention that an accurate determination of the total amount of hemoglobin in whole blood can be made not only without using a hemolysing agent but also without using a plurality of wavelengths as disclosed in the U.S. Pat. No. 6,262,798 or a special absorption or interference filter which provides correction for variations in the detector sensitivity and in the effective optical path length as observed upon varying level of scattering as disclosed in WO 01/53806 was therefore most unexpected.

OBJECTS OF THE INVENTION

An object of the present invention is to provide a rapid, quantitative method for the determination of hemoglobin in unaltered whole blood.

A second object is to provide a method for the determination of hemoglobin in unaltered whole blood, which may be performed in a disposable microcuvette.

A third object is to provide a cuvette with capillary inlet and without active reagents and hemolysing agent for the determination of hemoglobin in unaltered whole blood.

A fourth object is to provide a method of processing results of absorption measurements for determination of hemoglobin in unaltered whole blood.

A fifth object is to provide a system for implementing the methods for the determination of hemoglobin in unaltered whole blood.

Other objects will be apparent from the following description and the accompanying claims.

SUMMARY OF THE INVENTION

In accordance with an aspect of the present invention a method for providing such a hemoglobin determination comprises the steps of
- providing a disposable, capillary cuvette, which has an optical path length of less than 1 mm;
- filling said cuvette with a sample of unaltered whole blood;
- performing a first absorption measurement at a wavelength in the range 490–520 nm directly on the sample in the cuvette,
- further conducting a second absorption measurement, and
- processing results of the first and second absorption measurements to determine the concentration of hemoglobin in the sample, wherein the step of processing comprises compensating for scattering in the sample, said compensating being dependent on the result of the second absorption measurement.

According to another aspect of the present invention a method is provided for determining a concentration of hemoglobin in a sample of undiluted, unhemolyzed whole blood from a result of a first absorption measurement on the sample performed at a wavelength in the range 490–520 nm and a result of a second absorption measurement on the sample. The method comprises: processing the results of the first and second absorption measurements to determine the concentration of hemoglobin in the sample, wherein the step of processing comprises compensating for scattering in the sample, said compensating being dependent on the result of the second absorption measurement.

According to a further aspect of the present invention a system providing such a hemoglobin determination comprises:
- means for emitting light at a first wavelength in a first range of 490–520 nm and at a second wavelength in a second range,
- a cuvette holder arranged to receive a capillary cuvette, which has an optical path length of less than 1 mm and holds a sample of unaltered whole blood,
- a detector for detecting light transmitted through the sample in a first absorption measurement for light in said first range and in a second absorption measurement for light in said second range, and
- a processing unit for processing results of the first and second absorption measurements to determine the concentration of hemoglobin in the sample, wherein the processing comprises compensating for scattering in the sample, said compensating being dependent on the result of the second absorption measurement.

It has thus unexpectedly been found that quantitative determinations of hemoglobin can easily be performed without not only the chemical reagents sodium azide and sodium nitrite but also without a hemolysing agent directly on the unaltered, i.e. undiluted and unhemolysed, whole blood. Since the unaltered whole blood contains blood cells, there is substantial scattering of the light in the sample. Thus, it has heretofore been expected that a quantitative hemoglobin determination in undiluted, unhemolyzed whole blood would require detecting and analysing the scattered light. According to the invention, hemoglobin determination may be performed by two absorption measurements without the need for quantitatively knowing the scattering coefficients of the contents of the blood or physically reducing the measured effects of scattered light. It has unexpectedly been found that by compensating for the level of absorption of the sample in the second absorption measurement, the effect of scattering may easily be accounted for. Thus, according to the invention, hemoglobin determination is simple, requiring only two absorption measurements.

In accordance with the present invention it has thus been found that the hygroscopic reagents can be eliminated. Furthermore, it has been found that the time for obtaining the analytical determination may be reduced. As the analyses are performed in large amounts in e.g. hospitals and blood banks, the time aspect is important.

In the context of this application, the term "absorption measurement" should be construed as a measurement related to the absorption in a sample. In an absorption measurement, the intensity of light detected after interacting with a sample is compared with the intensity of light irradiated on the sample. The detected light corresponds to the transmittance through the sample. The light that does not reach the detector is considered to be absorbed. Thus, in the results of the measurements the transmittance may be used instead of the absorption. As the transmittance is the inverse of the absorption, detecting transmittance would still be an absorption measurement. However, the measured absorption does not only correspond to light that has been truly absorbed in the sample, since some of the light has been scattered in the sample so that it does not reach the detector.

Further, the term "determination" should be construed as the measurement not necessarily obtaining an absolutely exact value of the concentration of hemoglobin in the sample. Thus, the concentration of hemoglobin is "determined" within reasonable margins of error such that the result not merely gives an order of magnitude of the concentration, while not necessarily giving an absolute value.

BRIEF DESCRIPTION OF THE DRAWINGS

The invention will now by way of example be described in more detail with reference to the accompanying drawings, on which.

DETAILED DESCRIPTION OF THE INVENTION

Figure 1:
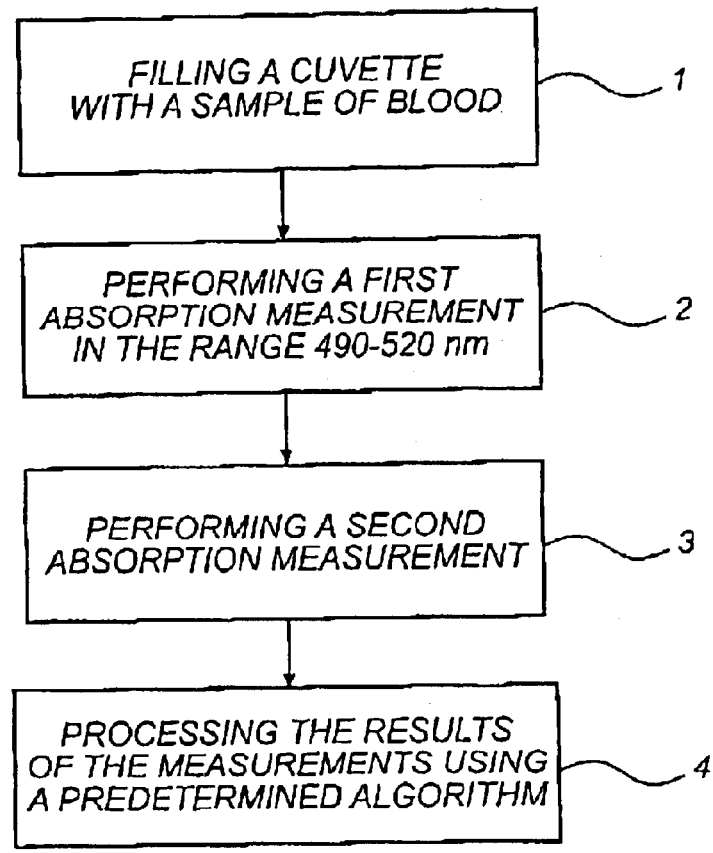
FIG. 1 is a flow chart of a method according to the invention.

Referring now to FIG. 1, a method for hemoglobin determination according to the invention will now be described. First, a disposable, capillary cuvette is filled with a sample of unaltered whole blood, step 1. Thus, a sample which is to be analysed is obtained. Then, a first absorption measurement on the sample is performed at a wavelength in the range 490–520 nm, step 2. Further, a second absorption measurement is performed on the sample, step 3. The second absorption measurement is performed at a wavelength in the range 650–1200 nm. This second absorption measurement is used to compensate for light scattering in the sample, as will be described in further detail below. Finally, the results of the measurements are processed, step 4, using a predetermined algorithm for determining the concentration of hemoglobin in the sample.

The disposable microcuvette used according to the present invention may be of the type disclosed in the U.S. Pat. No. 4,088,448 or preferably in the U.S. Pat. No. 5,674,457 which are hereby incorporated by reference. The cuvette may be defined as a unitary body member including at least one cavity with an optical window (measuring zone) wherein two, plane or curved, surfaces facing the cavity are placed at a predetermined distance from one another and thus define a predetermined optical path length. This distance between the surfaces defining the measuring zone is a critical parameter in providing the proper optical path length for the hemoglobin measurement. The optical path length should be less than 1 mm in order to ensure that the intensity of light transmitted through a sample in the cuvette is sufficient to enable determination of hemoglobin in the sample. In a preferred embodiment, this distance is less than 0.2 mm, and more preferably between 0.05 and 0.2 mm. The distance between the inner surfaces of the rest of the cavity is preferably in the order of 0.1–2 mm which is effective to permit the sample to enter the cavity by capillary force through the cavity inlet, which is communicating with the exterior of the body member. Furthermore, the cavity has a predetermined fixed volume of less than about 25 $\mu$l. No active additives, such as reagents or hemolysing agents, are necessary for the determination according to the inventive method.

The cuvettes according to the present invention may be formed by any suitable material, which allows the formation of the necessary tight tolerance levels. Preferably the cuvette is manufactured by injection moulding of a transparent polymeric material.

In order to overcome problems related to the capillary filling of the cuvette it may be necessary to pretreat the inner surfaces of the cuvette in order to impart a hydrophilic character to these surfaces. This may be achieved by coating the surfaces with a suitable detergent, such as Brij 35. Another possibility is to select a hydrophilic material for the manufacturing of the cuvette. A critical feature of the inventive method is that the absorption determination should be carried out at a wavelength in a range of 490–520 nm, more preferably in the range 500–510 nm, and most preferably at 506 nm. The secondary compensatory absorption measurement is preferably performed at a wavelength in the range 650–1200 nm, more preferably in the range 850–910 nm, and most preferably in the range 860–900 nm.

The absorption measurements are performed directly on the whole blood in the sample, i.e. the blood is unaltered (undiluted and unhemolyzed).

In the wavelength range of 490–520 nm, the absorptions of the five different forms of hemoglobin, namely oxy-, deoxy-, carboxy-, met- and sulfhemoglobin, are similar and significant. Thus, the absorption in this wavelength range will depend only slightly on the distribution between the different forms of hemoglobin in the blood. Especially, at 506 nm, the difference between the absorbances of oxy- and deoxyhemoglobin is close to zero. Since these forms of hemoglobin are predominant in normal blood, the absorption of oxy- and deoxyhemoglobin could advantageously be used for determining an absorption coefficient for relating a measured absorption to the concentration of hemoglobin at 506 nm. Accordingly, some assumptions are made regarding the contents of different forms of hemoglobin in the blood sample. Thus, the hemoglobin determination will not be as accurate or the processing of the measurement results will have to be modified, if a measurement is made on a blood sample having a very differing distribution of the forms of hemoglobin. Further, the measurements will only determine the total concentration of hemoglobin and not the concentrations of the specific forms of hemoglobin.

A second absorption measurement is performed at a wavelength, where the absorption of light in blood is substantially smaller. Such an absorption measurement could suitably be performed at a wavelength in the range 650–1200 nm. The differences between the absorption measurements is then considered to be due to absorption of hemoglobin.

Figure 2:
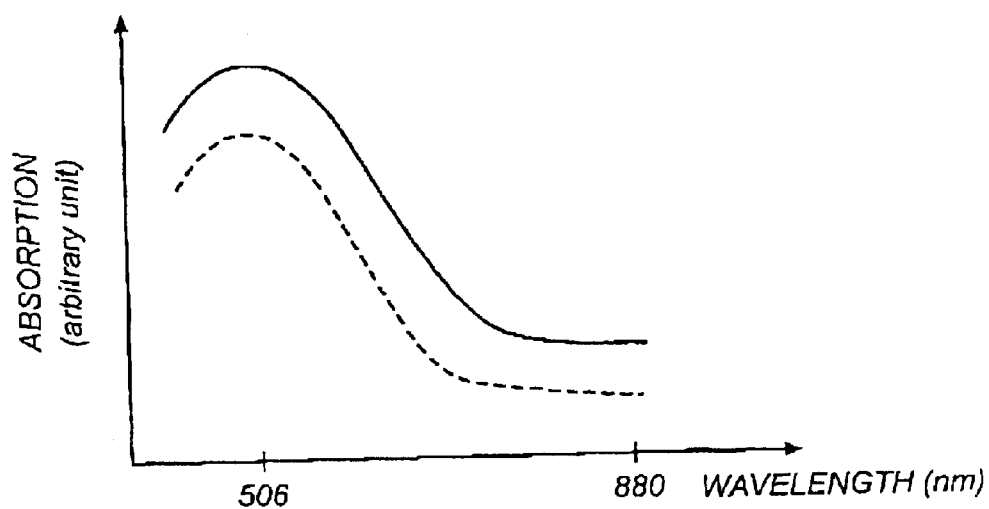
FIG. 2 is a schematic diagram of the absorbance of hemoglobin.

However, the scattering of light varies with the concentration of hemoglobin in the sample, but the scattering of light is not only dependent on the concentration of hemoglobin. The scattering of light is due to light interaction with particles in the blood, such as red blood cells, white blood cells, platelets, lipids and other macro molecules. According to the invention, it has unexpectedly been found that the effect of scattering may be related to the measured result in the second absorption measurement, as will be explained with reference to the schematic diagram in FIG. 2. In FIG. 2, the solid line schematically illustrates measured absorption in a first sample having a high concentration of hemoglobin. The absorption includes both true absorption and light scattered so that it does not reach a detector. The dashed line in FIG. 2 schematically illustrates measured absorption in a second sample having a lower concentration of hemoglobin. It should be noted that the schematic diagram in FIG. 2 only emphasizes the main features of absorption of samples of whole blood, and does not illustrate absorption of real samples. As can be seen in FIG. 2, the difference in absorption for the first sample between a first wavelength at 506 nm and a second wavelength at 880 nm is substantially equal to the corresponding difference in absorption for the second sample. Therefore, if the concentration of hemoglobin is determined directly from the differences in the measured absorptions, an erroneous result would be returned, at least for one of the samples. Thus, a compensation for the light scattering will be needed, and according to the invention it has been found that a compensation for the level of absorption will account for the scattering and enables simple hemoglobin determination.

It has empirically been determined that when using a compensation that is proportional to the level of absorption, a correct value of the concentration of hemoglobin may be obtained.

According to the above, the results of the absorption measurements should be processed for determining the concentration of hemoglobin in the sample. This processing may be performed by a predetermined algorithm. This algorithm calculates the concentration of hemoglobin according to the above-described scheme.

The compensation for light scattering is preferably dependent on the result of the second absorption measurement. A compensation function could be determined by performing absorption measurements on a set of blood samples having known concentrations of hemoglobin. These absorption measurements are performed in a measurement arrangement which is to be used. Then, the needed compensation for light scattering in order to obtain correct results are compared with the values of the second absorption measurement. In this way, a function of the second absorption measurement may be found that would give a compensation so that the determined concentrations of hemoglobin would fall within an acceptable margin of error.

In a simplified model, the compensation is linearly dependent on the result of the second absorption measurement at least in a range of the result of the second absorption measurement. This range of the result of the second absorption measurement may span typical values of the second absorption measurement that are obtained with the specific measurement arrangement.

The processing may determine the concentration of hemoglobin in the sample by computing the following formula:

$$[\text{Tot Hb}] = (\text{Abs}_1 - \text{Abs}_2) \cdot k + F(\text{Abs}_2)$$

wherein [Tot Hb] is the total concentration of hemoglobin in the sample, $\text{Abs}_1$ is the measured absorbance of the first absorption measurement, $\text{Abs}_2$ is the measured absorbance of the second absorption measurement, k is a calibration coefficient, which depends on the measurement arrangement, and $F(\text{Abs}_2)$ is a function that depends on the measured absorbance of the second absorption measurement. The calibration coefficient k may be specific for each instrument used for hemoglobin determination. The compensating function $F(\text{Abs}_2)$ may have a constant part, which also is a calibration for each instrument, and a variable part, which depends on the result of the second absorption measurement and is obtained as described above. In this case, the variable part may be zero for a result of the second absorption measurement that is in the centre of the range of the results of the second absorption measurement.

Figure 3:
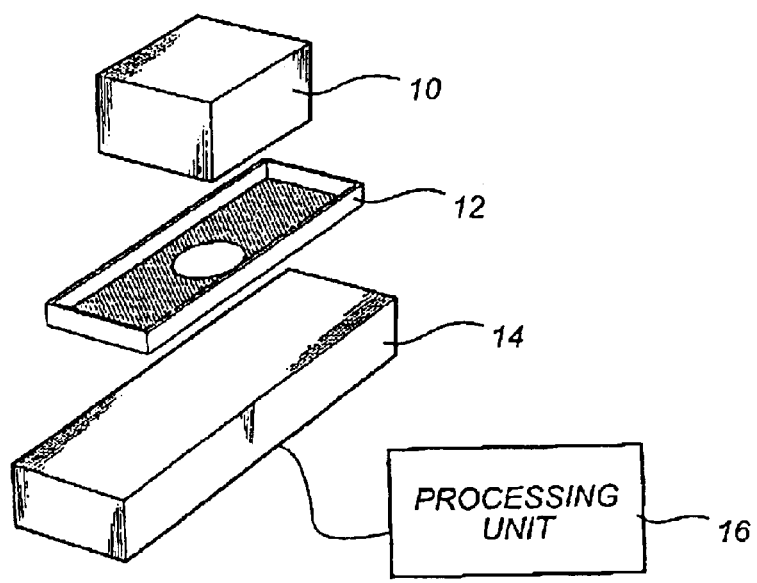
FIG. 3 is a schematic view of a system according to the invention.

Referring now to FIG. 3, a system implementing the above-described method will be described. The system comprises means 10 for emitting light at a first wavelength in a first range of 490–520 nm and at a second wavelength in a second range of 650–1200 nm. This means 10 for emitting light may be implemented by a combination of a light source emitting at several wavelengths or in broad wavelength ranges together with filters. Thus, the light source is arranged to emit light both at the first wavelength and at the second wavelength. Using the filter the wavelength emitted could selectively be controlled to be within one of these ranges. Alternatively, a first and a second light source may be used for emitting the first and the second wavelengths, respectively. Light emitting diodes may be used as light sources. Then, by switching the two light sources on and off, the means 10 for emitting light may be selectively controlled to emit light in the first or in the second wavelength.

Preferably, the first wavelength emitted by the means 10 for emitting light is in the range 500–510 nm, more preferably at 506 nm. Further, the second wavelength emitted by the means 10 for emitting light is preferably in the range 850–910 nm, and more preferably in the range 860–900 nm.

The system further comprises a cuvette holder 12 arranged to receive a capillary cuvette, which has an optical path length of less than 1 mm and holds a sample of unaltered whole blood. When a cuvette is placed in the holder 12, the optical window will be correctly positioned so that it will be irradiated with the light from the light source. Preferably, the cuvette holder is arranged to receive a cuvette, which has an optical path length of less than 0.2 mm, and more preferably in the range 0.05–0.2 mm.

The light transmitted through the sample will be detected by a detector 14 so that a first absorption measurement may be obtained for light in the first range and a second absorption measurement may be obtained for light in the second range.

The system further comprises a processing unit 16 for processing results of the first and second absorption measurements to determine the concentration of hemoglobin in the sample according to the algorithm described above.

The system may suitably be implemented in a photometer comprising the means 10 for emitting light, the cuvette holder 12, and the detector 14. Photometers suitable for performing these measurements may be obtained by using photometers modified with suitable wave length filters and light emitting diodes. According to a preferred embodiment of the invention a photometer measures the absorbance at the two wavelengths and a built-in micro processor calculates, according to a programmed algorithm, the total concentration of hemoglobin in blood. Thus, no special absorption or interference filter which provide correction for variations in the detector sensitivity and in the effective optical path length as disclosed in WO 01/53806 are necessary.

In the above case, the processing unit 16 is embedded in the photometer. However, the processing unit 16 may also be connected to the photometer, and thus be implemented outside the photometer. For example, a computer connected to the photometer may be used.

The detector 14 may be arranged to detect essentially only directly transmitted light, since the scattered light need not be detected. This implies that the detector 14 detects light which is essentially within the diameter of the light beam irradiated on the sample and directly transmitted through the sample. Of course, some light may be scattered, while still being within this diameter. According to a preferred embodiment, the diameter of a detecting area of the detector 14 may typically be approximately 2 mm. The detector 14 is preferably arranged closer than 10 mm to the sample holder. This implies that light which has been scattered to small angles is detected.

The following non limiting example illustrates the inventive method.

It was found that the time period for analysing the blood was about 30 seconds shorter for the inventive method in a comparison with the method for determination of hemoglobin in the known, currently used HemoCue microcuvettes. This permits a clear reduction of the total time of the hemoglobin determination which may be advantageous in busy hospitals and in other situations where may determinations are made. Another advantage is that there is no need for a cuvette containing active reagents or hemolysing agents. Thus, storage of the cuvettes is insensitive to temperature and humidity in the storage environment, which makes handling of the cuvettes before their use much simpler.

Figure 4A:
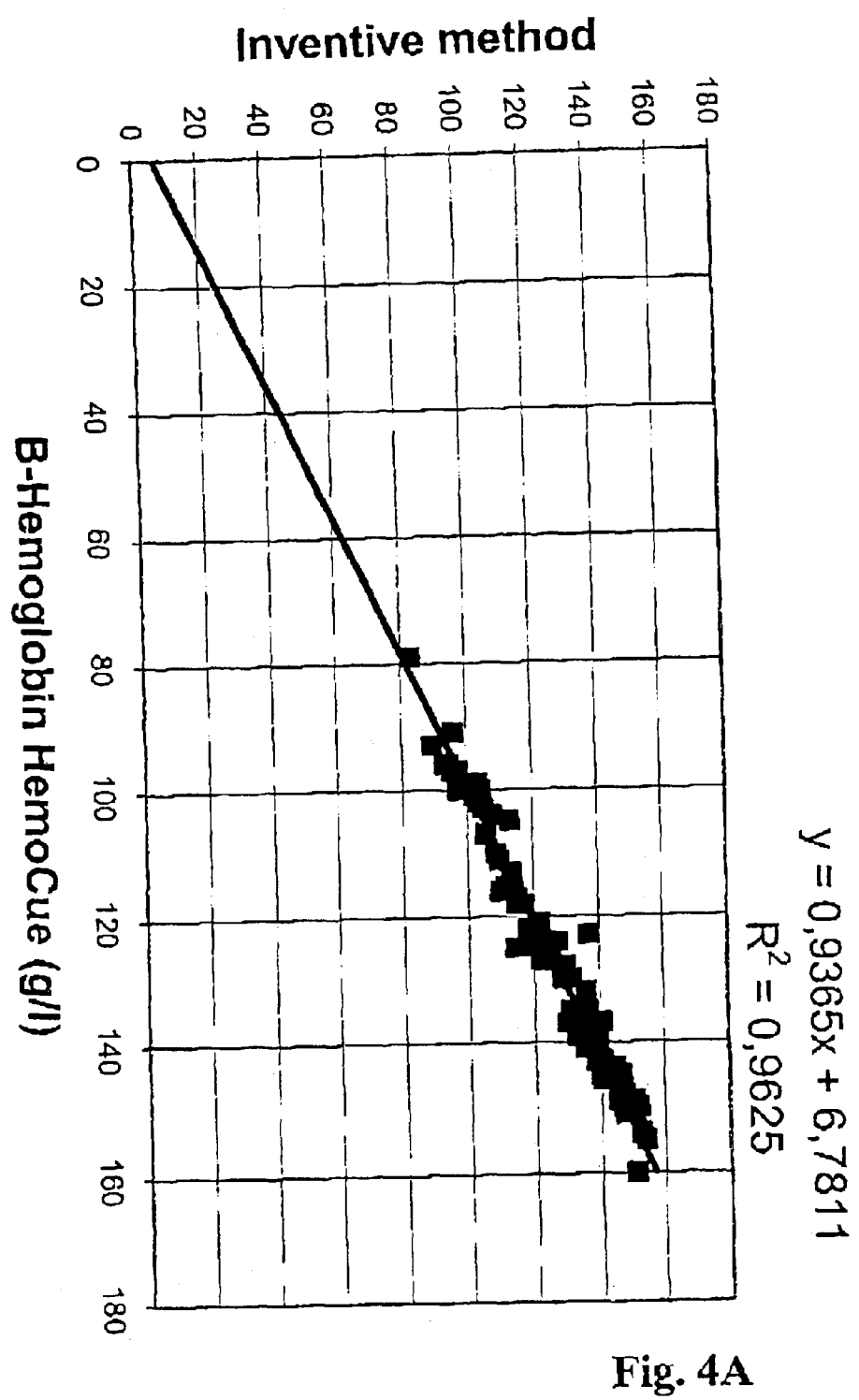
FIG. 4A is a diagram illustrating a preliminary evaluation of the inventive method in comparison with currently used HemoCue microcuvettes.

A preliminary evaluation of the new method in comparison with the HemoCue method is disclosed in FIG. 4A. The evaluation was made under laboratory conditions. As can be seen the agreement between the methods is very good.

The spectrophotometric absorption measurements were made at about 570 nm for the known method and about 505 nm for the new method. For both methods compensatory measurements were made at about 880 nm.

Figure 4B:
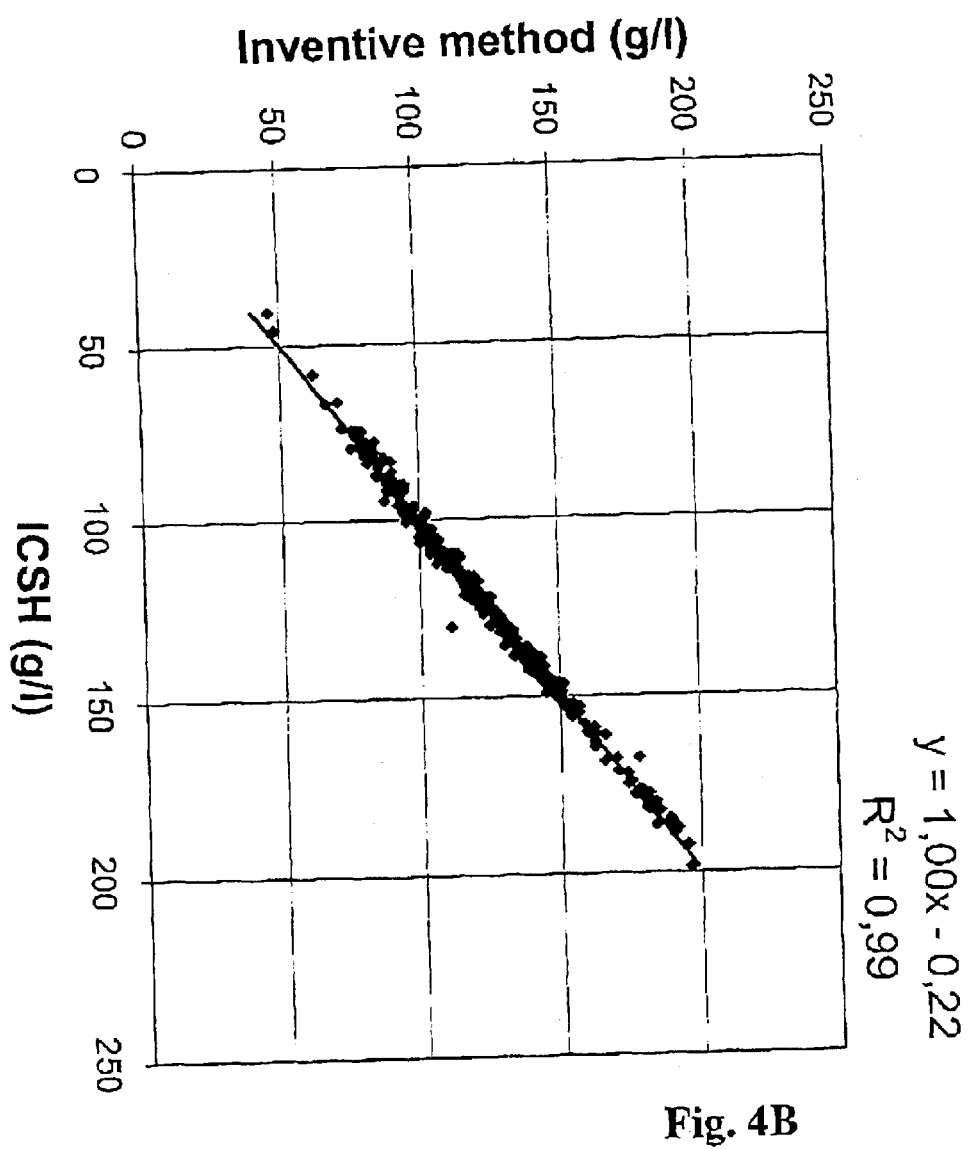
FIG. 4B is a diagram illustrating a preliminary evaluation of the inventive method in comparison with an international reference method.

Further, a second evaluation of the new method in comparison with the standard ICSH method is disclosed in FIG. 4B. As can be seen the agreement between these methods is also very good.

The foregoing has been a description of a certain preferred embodiment of the present invention, but it is not intended to limit the invention in any way. Rather, many modifications, variations, and changes in details may be made within the scope of the present invention.

What is claimed is:

1. A method for quantitative hemoglobin determination in undiluted, unhemolyzed whole blood comprising the steps of:

providing a disposable, capillary curvette, which has an optical path length of less than 1 mm;

filling said cuvette with a sample of unaltered whole blood;

performing a first absorption measurement at a wavelength in the range 490–520 nm directly on the sample in the cuvette, further conducting a second absorption measurement, and processing results of the first and second absorption measurements to determine the concentration of hemoglobin in the sample, wherein the step of processing comprises compensating for scattering in the sample, said compensating being dependent on the result of the second absorption measurement.

2. The method according to claim 1 wherein the first absorption measurement is performed at a wavelength in the range 500–510 nm.

3. The method according to claim 1 wherein the second absorption measurement is performed at a wavelength in the range 650–1200 nm.

4. The method according to claim 1 wherein the absorption measurement is performed in a photometer without an absorption filter or an interference filter, which provide correction for variations in the detector sensitivity and in the effective optical path length.

5. The method according to claim 1 wherein said cuvette has an optical path length of less than 0.2 mm.

6. The method according to claim 5 wherein said cuvette has an optical path length in the range 0.05–0.2 mm.

7. The method according to claim 1 wherein said processing is performed by a predetermined algorithm.

8. The method according to claim 7 wherein said processing determines the concentration of hemoglobin in the sample by computing the following formula:

$$[\text{Tot Hb}] = (\text{Abs}_1 - \text{Abs}_2) \cdot k + F(\text{Abs}_2)$$

wherein [Tot Hb] is the total concentration of hemoglobin in the sample, $\text{Abs}_1$ is the measured absorbance of the first absorption measurement, $\text{Abs}_2$ is the measured absorbance of the second absorption measurement, k is a calibration coefficient, which depends on the measurement arrangement, and $F(\text{Abs}_2)$ is a function that depends on the measured absorbance of the second absorption measurement.

9. The method according to claim 1 wherein the first absorption measurement is performed at a wavelength of 506 nm.

10. The method according to claim 1 wherein the second absorption measurement is performed at a wavelength in the range 850–910 nm.

11. The method according to claim 1 wherein the second absorption measurement is performed at a wavelength in the range 860–900 nm.

12. A method for determining a concentration of hemoglobin in a sample of undiluted, unhemolyzed whole blood from a result of a first absorption measurement on the sample performed at a wavelength in the range 490–520 nm and a result of a second absorption measurement on the sample, said method comprising:

processing the results of the first and second absorption measurements to determine the concentration of hemoglobin in the sample, wherein the step of processing comprises compensating for scattering in the sample, said compensating being dependent on the result of the second absorption measurement.

13. The method according to claim 12 wherein said processing determines the concentration of hemoglobin in the sample by computing the following formula:

$$[\text{Tot Hb}] = (\text{Abs}_1 - \text{Abs}_2) \cdot k + F(\text{Abs}_2)$$

wherein [Tot Hb] is the total concentration of hemoglobin in the sample, $\text{Abs}_1$ is the measured absorbance of the first absorption measurement, $\text{Abs}_2$ is the measured absorbance of the second absorption measurement, k is a calibration coefficient, which depends on the measurement arrangement, and $F(\text{Abs}_2)$ is a function that depends on the measured absorbance of the second absorption measurement.

14. The method according to claim 12 wherein the first absorption measurement is performed at a wavelength in the range 500–510 nm.

15. The method according to claim 12 wherein the second absorption measurement is performed at a wavelength in the range 650–1200 nm.

16. The method according to claim 12 wherein the first absorption measurement is performed at a wavelength in the range of 506 nm.

17. The method according to 12 wherein the second absorption measurement is performed at a wavelength in the range 850–910 nm.

18. The method according to claim 12 wherein the second absorption measurement is performed at a wavelength in the range 860–900 nm.

19. A system for quantitative hemoglobin determination in undiluted, unhemolyzed whole blood comprising:

means for emitting light at a first wavelength in a first range of 490–520 nm and at a second wavelength in a second range, a cuvette holder arranged to receive a capillary cuvette, which has an optical path length of less than 1 mm and holds a sample of unaltered whole blood, a detector for detecting light transmitted through the sample in a first absorption measurement for light in said first range and in a second absorption measurement for light in said second range, and a processing unit for processing results of the first and second absorption measurements to determine the concentration of hemoglobin in the sample, wherein the processing comprises compensating for scattering in the sample, said compensating being dependent on the result of the second absorption measurement.

20. The system according to claim 19 wherein said means for emitting light, cuvette holder and detector are arranged in a photometer.

21. The system according to claim 20 wherein said processing unit is embedded in the photometer.

22. The system according to claim 20 wherein said processing unit is connected to the photometer.

23. The system according to claim 19 wherein a detecting area of the detector has a size such that essentially only directly transmitted light is detected.

24. The system according to claim 19 wherein the detector is arranged closer than 10 mm to the sample holder.

25. The system according to claim 19 wherein said means for emitting light comprises one light source, which is arranged to emit light at the first wavelength and to emit light at the second wavelength.

26. The system according to claim 19 wherein the means for emitting light comprises a first light source, which is arranged to emit light at the first wavelength, and a second light source, which is arranged to emit light at the second wavelength.

27. The system according to claim 19 wherein the first wavelength emitted by the means for emitting light is in the range 500–510 nm.

28. The system according to claim 19 wherein the second wavelength emitted by the means for emitting light is in the range 650–1200 nm.

29. The system according to claim 19 wherein the cuvette holder is arranged to receive a cuvette, which has an optical path length of less than 0.2 mm.

30. The system according to claim 29 wherein the cuvette holder is arranged to receive a cuvette, which has an optical path length in the range 0.05–0.2 mm.

31. The system according to claim 19 wherein said processing unit uses a predetermined algorithm for performing said processing.

32. The method according to claim 31 wherein said processing determines the concentration of hemoglobin in the sample by computing the following formula:

$$[\text{Tot Hb}] = (\text{Abs}_1 - \text{Abs}_2) \cdot k + F(\text{Abs}_2).$$

33. The system according to claim 19 wherein the first wavelength emitted by the means for emitting light is at a wavelength of 506 nm.

34. The system according to claim 19 wherein the second wavelength emitted by the means for emitting light is in the range 850–900 nm.

35. The system according to claim 19 wherein the second wavelength emitted by the means for emitting light is in the range 860 to 900 nm.

* * * * *